United States Patent [19]

Stetter et al.

[11] Patent Number: 4,489,081
[45] Date of Patent: Dec. 18, 1984

[54] FUNGICIDALLY ACTIVE NOVEL SUBSTITUTED AZOLYLETHYL OXIMINOALKYL ETHERS

[75] Inventors: Jörg Stetter, Wuppertal; Karl H. Büchel, Burscheid; Paul Reinecke, Leverkusen; Wilhelm Brandes, Leichlingen; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 468,820

[22] Filed: Feb. 22, 1983

[30] Foreign Application Priority Data

Mar. 6, 1982 [DE] Fed. Rep. of Germany ....... 3208194

[51] Int. Cl.³ .................. A01N 43/64; A01N 43/48; C07D 233/60; C07D 249/08
[52] U.S. Cl. ................................ 424/269; 548/262
[58] Field of Search ..................... 424/269; 548/262

[56] References Cited

U.S. PATENT DOCUMENTS

| | | | |
|---|---|---|---|
| 3,896,189 | 7/1975 | Stach | 424/211 |
| 4,327,104 | 4/1982 | Timmler et al. | 424/232 |
| 4,344,953 | 8/1982 | Stetter et al. | 548/262 |
| 4,366,152 | 12/1982 | Kramer et al. | 548/262 |

FOREIGN PATENT DOCUMENTS 1940388  2/1970  Fed. Rep. of Germany .
2613167  10/1977  Fed. Rep. of Germany .

OTHER PUBLICATIONS

Chem. Abst. 100, 6525e (1984) Stetter et al.

*Primary Examiner*—Douglas W. Robinson
*Attorney, Agent, or Firm*—Sprung, Horn, Kramer & Woods

[57] ABSTRACT

Fungicidally active novel substituted azolylethyl oximinoalkyl ethers of the formula

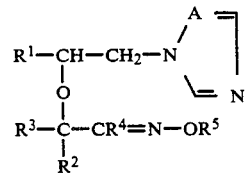

in which
 A is a nitrogen atom or the CH group,
 $R^1$ is optionally substituted phenyl,
 $R^2$, $R^3$ and $R^4$ each independently is hydrogen, alkyl or optionally substituted phenyl, and
 $R^5$ is hydrogen, alkyl, alkenyl, alkinyl, optionally substituted phenyl or optionally substituted phenylalkyl,
or addition products thereof with acids or metal salts.

7 Claims, No Drawings

FUNGICIDALLY ACTIVE NOVEL SUBSTITUTED AZOLYLETHYL OXIMINOALKYL ETHERS

The present application relates to new substituted azolylethyl oximinoalkyl ethers, a process for their preparation, and their use as fungicides.

It has already been disclosed that certain triazolylether-ether derivatives, such as, for example, [1-(4-chlorophenyl)-2-(1,2,4-triazol-1-yl)]-ethyl allyl ether and [1-(2,4-dichlorophenyl)-2-(1,2,4-triazol-1-yl)]-ethyl n-butyl ether possess generally good fungicidal properties (see U.S. Pat. No. 4,327,104). However, the action of these compounds is not always completely satisfactory in certain fields of indication, in particular when low amounts and concentrations are used.

New substituted azolylethyl oximinoalkyl ethers of the general formula $$R^1-CH-CH_2-N\underset{\underset{N}{\diagdown}}{\overset{\overset{A \,=\!=}{\diagup}}{\Big|}} \quad (I)$$
$$\underset{R^2}{\overset{O}{|}} \quad$$
$$R^3-C-CR^4=N-OR^5$$

in which
 A represents a nitrogen atom or the CH group,
 $R^1$ represents optionally substituted phenyl,
 $R^2$ represents hydrogen, alkyl or optionally substituted phenyl,
 $R^3$ represents hydrogen, alkyl or optionally substituted phenyl,
 $R^4$ represents hydrogen, alkyl or optionally substituted phenyl and
 $R^5$ represents hydrogen, alkyl, alkenyl, alkinyl, optionally substituted phenyl or optionally substituted phenylalkyl.
and their acid addition salts and metal salt complexes have been found.

The compounds of the formula (I) can be present in the syn form or anti form; they are obtained predominantly as mixtures of both forms.

Furthermore, it has been found that the substituted azolylethyl oximinoalkyl ethers of the formula (I) and their acid addition salts and metal salt complexes are obtained when azolylethanols of the formula $$R^1-\underset{\underset{}{|}}{\overset{OH}{C}}H-CH_2-N\underset{\underset{N}{\diagdown}}{\overset{\overset{A \,=\!=}{\diagup}}{\Big|}} \quad (II)$$

in which
 A and $R^1$ have the meanings given above,
are reacted with oxime derivatives of the formula $$Z-\underset{R^3}{\overset{R^2}{\underset{|}{\overset{|}{C}}}}-CR^4=N-OR^5 \quad (III)$$

in which
 $R^2$, $R^3$, $R^4$ and $R^5$ have the meaning given above and
 Z represents halogen, the methylsulphonyloxy radical or the tolylsulphonyloxy radical, in the presence of a base and in the presence of an organic diluent, or in an aqueous-organic two-phase system in the presence of a phase-transfer catalyst; and if appropriate an addition product with an acid or a metal salt is then formed.

The new substituted azolylethyl oximinoalkyl ethers of the formula (I) possess powerful fungicidal properties. In this context, the compounds according to the invention surprisingly exhibit a better fungicidal action than the triazolyl-ethyl-ether derivatives, such as, for example, [1-(4-chlorophenyl)-2-(1,2,4-triazol-1-yl)]-ethyl allyl ether and [1-(2,4-dichlorophenyl)-2-(1,2,4-triazol-1-yl)]ethyl n-butyl ether, which are known from the prior art and are similar compounds chemically and in terms of their action. The substances according to the invention thus represent an enrichment of the art.

Formula (I) gives a general definition of the substituted azolylethyl oximinoalkyl ethers according to the invention. In this formula,
 A preferably represents a nitrogen atom or the CH group;
 $R^1$ preferably represents phenyl which is optionally monosubstituted or disubstituted by identical or different substituents, the following being preferably mentioned as substituents: halogen, alkyl having 1 to 4 carbon atoms, alkoxy having 1 to 2 carbon atoms and halogenoalkyl and halogenoalkoxy, each having 1 to 2 carbon atoms and 1 to 5 identical or different halogen atoms, such as fluorine atoms and chlorine atoms;
 $R^2$ preferably represents hydrogen, alkyl having 1 to 4 carbon atoms, and phenyl which is optionally monosubstituted or disubstituted by identical or different substituents, the phenyl substituents already mentioned in the case of $R^1$ being preferred substituents;
 $R^3$ preferably represents hydrogen, alkyl having 1 to 4 carbon atoms, and phenyl which is optionally monosubstituted or disubstituted by identical or different substituents, the phenyl substituents already mentioned in the case of $R^1$ being preferred substituents;
 $R^4$ preferably represents hydrogen, alkyl having 1 to 4 carbon atoms, and phenyl which is optionally monosubstituted or disubstituted by identical or different substituents, the phenyl substituents already mentioned in the case of $R^1$ being preferred substituents; and
 $R^5$ preferably represents hydrogen, alkyl having 1 to 4 carbon atoms, alkenyl and alkinyl, each having 2 to 4 carbon atoms, and phenyl and phenylalkyl having 1 to 2 carbon atoms in the alkyl part, each of which is optionally monosubstituted or disubstituted by identical or different substituents, the phenyl substituents already mentioned in the case of $R^1$ being preferred substituents in the aromatic radicals.

Particularly preferred compounds of the formula (I) are those
in which
 A represents a nitrogen atom or the CH group;
 $R^1$ represents a phenyl which is optionally monosubstituted or disubstituted by identical or different substituents, the following being particularly mentioned as substituents: fluorine, chlorine, bromine, methyl, ethyl, methoxy, trifluoromethyl and trifluoromethoxy;

R² represents hydrogen, methyl, ethyl and isopropyl, and represents phenyl which is optionally mono-substituted or disubstituted by identical or different substituents, the phenyl substituents already mentioned in the case of R¹ being particularly preferred substituents;

R³ represents hydrogen, methyl, ethyl and isopropyl, and represents phenyl which is optionally mono-substituted or disubstituted by identical or different substituents; the phenyl substituents already mentioned in the case of R¹ being particularly suitable substituents;

R⁴ represents hydrogen, methyl, ethyl and isopropyl, and represents phenyl which is optionally mono-substituted or disubstituted by identical or different substituents, the phenyl substituents already mentioned in the case of R¹ being particularly suitable substituents; and R⁵ represents hydrogen, methyl, ethyl, isopropyl, n-propyl, n-butyl, sec.-butyl, tert.-butyl, vinyl, allyl and propargyl, and represents phenyl and benzyl, each of which is optionally monosubstituted or disubstituted by identical or different substituents, the phenyl substituents already mentioned in the case of R¹ being particularly suitable substituents.

Addition products of acids and those substituted azolylethyl oximinoalkyl ethers of the formula (I) in which the substituents A, R¹, R², R³, R⁴ and R⁵ have the meanings which have already been mentioned as being preferred for these radicals are also preferred compounds according to the invention.

The acids which can be used to form addition products preferably include hydrohalic acids, such as, for example, hydrochloric acid, and also phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, salicylic acid, sorbic acid and lactic acid, and sulphonic acids, such as, for example, p-toluenesulphonic acid and naphthalene-1,5-disulphonic acid.

Further preferred compounds according to the invention are addition products of salts of metals of main groups II to IV and of sub-groups I and II and IV to VIII and those substituted azolylethyl oximinoalkyl ethers of the formula (I) in which the substituents A, R¹, R², R³, R⁴ and R⁵ have the meanings which have already been mentioned as being preferred for these radicals. In this context, salts of copper, zinc, manganese, magnesium, tin, iron and nickel are particularly preferred. Suitable anions of these salts are those which are derived from those acids which give physiologically tolerated addition products. In this connection, particularly preferred acids of this type are hydrohalic acids, such as, for example, hydrochloric acid and hydrobromic acid.

If, for example 1-(2,4-dichlorophenyl)-2-(1,2,4-triazol-1-yl)-ethanol and 1-chloro-2-methoximino-2-phenylethane are used as starting materials, the course of the reaction of the process according to the invention can be represented by the following equation:

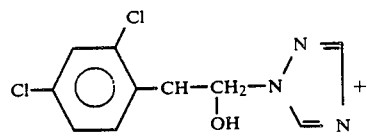

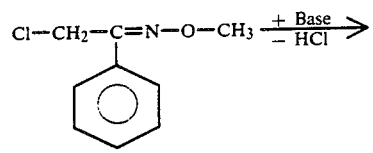

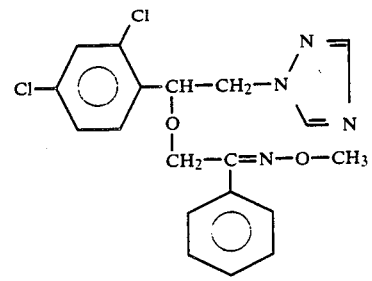

Formula (II) gives a general definition of the azolylethanols required as starting materials in carrying out the process according to the invention. In this formula, A and R¹ preferably have the meanings which have already been mentioned in the description of the substances according to the invention, of the formula (I), as being preferred.

Azolylethanols of the formula (II) are known (see, for example, DE-OS (German Published Specifications Nos. 2,431,407, 2,638,470 and 1,940,388); they can be obtained in a generally known manner, by reacting the appropriate α-bromo(chloro)-ketones with imidazole or 1,2,4-triazole in the presence of an inert organic solvent, such as, for example, acetone, and in the presence of an acid-binding agent, such as, for example, potassium carbonate, preferably at the boil, and reducing the resulting azolylethanones in a conventional manner with complex hydrides, such as, for example, sodium borohydride, or with aluminum isopropylate.

Formula (III) gives a general definition of the oxime derivatives additionally to be used as starting materials for the process according to the invention. In this formula, R², R³, R⁴ and R⁵ preferably have the meanings which have already been mentioned in the description of the substances according to the invention, of the formula (I), as being preferred. Z preferably represents chlorine, bromine, the methylsulphonyloxy radical and the tolylsulphonyloxy radical. Oxime derivatives of the formula (III) are known (see, for example, U.S. Pat. No. 3,896,189 and DE-OS (German Published Specification) No. 2,922,759); they can be obtained in a generally known manner, by reacting the corresponding carbonyl compounds with hydroxylamine (derivatives) in the presence of a solvent, preferably an alcohol, at temperatures between 20° C. and 100° C., preferably between 50° C. and 80° C. In this reaction, the hydroxylamine (derivative) is preferably employed in the form of a salt, in particular as the hydrochloride, if appropriate in the presence of an acid-binding agent, such as, for example, sodium acetate. The end products are isolated in a conventional manner. Individual oxime derivatives of the formula (III) can also be obtained when oxime-ethers of the formula $$R^3-CH_2-CR^4=N-OR^5 \quad (IV)$$

in which $R^3$, $R^4$ and $R^5$ have the meaning given above, are halogenated in a customary manner (in this context, see J. Org. Chem. 36, (1971) 3467).

Preferred diluents for the process according to the invention are inert organic solvents. These preferably include ketones, such as diethyl ketone, in particular acetone and methyl ethyl ketone; nitriles, such as propionitrile, in particular acetonitrile; ethers, such as tetrahydrofuran or dioxane; aliphatic and aromatic hydrocarbons, such as petroleum ether, benzene, toluene or xylene; halogenated hydrocarbons, such as methylene chloride, carbon tetrachloride, chloroform or chlorobenzene; and esters, such as ethyl acetate. All customary organic and inorganic bases can be employed as bases for the process according to the invention. These preferably include tertiary amines, for example triethylamine, or pyridine and alkali metal hydroxides or alkali metal carbonates, for example sodium hydroxide and potassium hydroxide, and alkali metal hydrides, such as, for example, sodium hydride.

In carrying out the process according to the invention, the reaction temperatures can be varied within a relatively wide range. In general, the reaction is carried out at between 0° C. and 150° C., preferably between 20° C. and 100° C.

In carrying out the process according to the invention, equimolar amounts are preferably employed. However, it is also possible to employ an excess of one of the components. Working-up and isolation of the reaction products are effected according to customary methods.

In a preferred embodiment, the reaction according to the invention is carried out in a two-phase system, such as, for example, aqueous sodium hydroxide or potassium hydroxide solution/toluene or methylene chloride, if appropriate with the addition of 0.1-1 mol of a phase-transfer catalyst, such as, for example, an ammonium or phosphonium compound, benzyldodecyl-dimethylammonium chloride and triethylbenzyl-ammonium chloride being mentioned as examples.

Preferred acids for the preparation of acid addition salts of the compounds of the formula (I) are those which have already been mentioned in connection with the description of the acid addition salts according to the invention as being preferred acids.

The acid addition salts of the compounds of the formula (I) can be obtained in a simple manner by customary salt formation methods, by dissolving a compound of the formula (I) in a suitable solvent and adding the acid, for example hydrochloric acid, and can be isolated in a known manner, for example by filtration and if appropriate purified by washing with an inert organic solvent. Preferred salts for the preparation of metal salt complexes of compounds of the formula (I) are salts of those anions and cations which have already been mentioned in connection with the description of the metal salt complexes according to the invention as being preferred.

The metal salt complexes of compounds of the formula (I) can be obtained in a simple manner by customary processes, thus, for example, by dissolving the metal salt in an alcohol, for example ethanol, and adding the solution to the compound of the formula (I). Metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases, thus, for combating Erysiphe species, such as, for example, against the powdery mildew of barley causative organism (*Erysiphe graminis*), Leptosphaeria species, such as, for example, against the leaf spot disease of wheat causative organism (*Leptosphaeria nodorum*), Sphaerotheca species, such as, for example, against the powdery mildew of cucumber causative organism (*Sphaerotheca fuliginea*), and Podosphaera species, such as, for example, against the powdery mildew of apple causative organism (*Podosphaera Leucotricha*); in addition, for combating rice diseases, such as, for example, *Pyricularia oryzae* and *Pellicularia sasakii*.

When used in appropriate amounts, the substances according to the invention also exhibit herbicidal activity.

The active compounds can be converted to the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating-compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant those liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates; as solid carriers for granules there are suitable: for example crushed and fractionated natural rocks such as calcite, marble, pumice, sepiolite and dolomite, as well as synthetic granules of inorganic and organic metals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or of the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

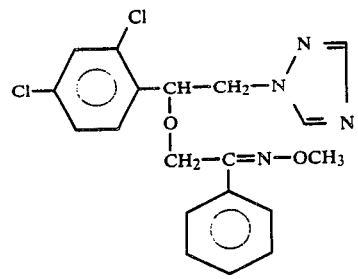

12.9 g (0.05 mol) of 1-(2,4-dichlorophenyl)-2-(1,2,4-triazol-1-yl)-ethanol in a two-phase system comprising 150 ml of methylene chloride and 30 ml of 50% strength sodium hydroxide solution, with the addition of 150 g of triethyl-benzyl-ammonium chloride, are stirred vigorously, and 11 g (0.06 mol) of 1-chloro-2-methoximino-2-phenyl-ethane are added dropwise. The reaction mixture is stirred for 6 hours at 42° C., and the organic phase is separated off, washed neutral with water and dried over sodium sulphate. Thereafter, the solvent is separated off in vacuo and the residue is degassed in a high vacuum. After trituration with petroleum ether, the residue crystallizes out. 8.2 g (41% of theory) of 1-(2,4-dichlorophenyl)-1-(2-methoximino-2-phenyl-ethoxy)-2-(1,2,4-triazol-1-yl)-ethane of melting point 82°–84° C. are obtained.

Preparation of the starting material

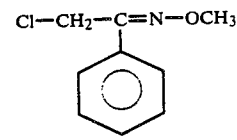

46.3 g (0.3 mol) of ω-chloroacetophenone, 27.5 g (0.33 mol) of O-methyl-hydroxylamine hydrochloride and 27 g (0.33 mol) of sodium acetate in ethanol are heated under reflux for 3 hours. Thereafter, the inorganic precipitate is filtered off and the filtrate concentrated. The residue is partitioned between water and methylene chloride, and the organic phase is separated off, dried over sodium sulphate and concentrated. The residue is distilled in a high vacuum. 44 g (80% of theory) of 1-chloro-2-methoximino-2-phenyl-ethane of boiling point 65° C./0.3 mbar are obtained.

The compounds in the following table, of the general formula

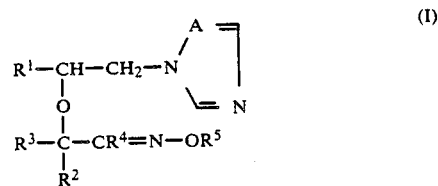

are obtained in a corresponding manner and in accordance with the process according to the invention:

| Example No. | R¹ | R² | R³ | R⁴ | R⁵ | A | Physical constant |
|---|---|---|---|---|---|---|---|
| 2 | 4-Cl-C₆H₄- | H | H | H | CH₃ | N | b.p.: 180° C./0.1 mbar |
| 3 | 2,4-Cl₂-C₆H₃- | H | H | H | CH₃ | N | $n_D^{20}$: 1.5555 |
| 4 | 4-Br-C₆H₄- | H | H | H | CH₃ | N | b.p.: 190° C./0.1 mbar |
| 5 | 2,4-Cl₂-C₆H₃- | H | CH₃ | H | CH₃ | N | m.p.: 90–113° C. |
| 6 | 2,4-Cl₂-C₆H₃- | H | H | CH₃ | CH₃ | N | b.p.: 190° C./0.2 mbar |
| 7 | 2,4-Cl₂-C₆H₃- | H | CH₃ | CH₃ | CH₃ | N | viscous oil |
| 8 | 2,4-Cl₂-C₆H₃- | H | H | H | CH₃ | CH | b.p.: 170° C./0.2 mbar |
| 9 | 2,4-Cl₂-C₆H₃- | H | CH₃ | H | CH₃ | CH | b.p.: 160° C./0.1 mbar |
| 10 | 2,4-Cl₂-C₆H₃- | H | H | CH₃ | CH₃ | CH | viscous oil |
| 11 | 2,4-Cl₂-C₆H₃- | H | H | C₆H₅- | CH₃ | CH | viscous oil |
| 12 | 2,4-Cl₂-C₆H₃- | H | H | C₆H₅- | CH₃ | CH | m.p.: 186–88° C. (× ½ NDA) |

-continued

| Example No. | R¹ | R² | R³ | R⁴ | R⁵ | A | Physical constant |
|---|---|---|---|---|---|---|---|
| 13 | 2,4-dichlorophenyl | H | CH₃ | CH₃ | CH₃ | CH | viscous oil |
| 14 | 2,4-dichlorophenyl | H | CH₃ | H | C₂H₅ | CH | b.p.: 170° C./ 0.2 mbar |
| 15 | 2,4-dichlorophenyl | H | H | 4-chlorophenyl | CH₃ | N | m.p.: 78° C. |
| 16 | 2,4-dichlorophenyl | H | H | 4-methoxyphenyl | CH₃ | N | viscous oil |
| 17 | 2,4-dichlorophenyl | H | H | 2,4-dichlorophenyl | CH₃ | N | $n_D^{20} = 1.5864$ |
| 18 | 2,4-dichlorophenyl | H | H | 4-bromophenyl | CH₃ | N | m.p.: 128–30 |

*NDA = naphthalene-1,5-disulphonic acid

USE EXAMPLES

The compounds given below are employed as comparative substances in the examples which follow:

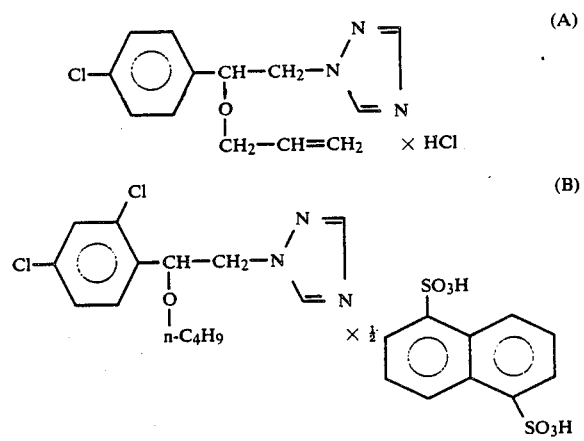

Example A

Erysiphe test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of Erysiphe graminis f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: 3, 4, 8, 9 and 6.

Example B

Erysiphe test (barley)/seed treatment

The active compounds are used as dry dressings. These are prepared by extending the particular active compound with a ground mineral to give a finely pulverulent mixture, which ensures uniform distribution on the seed surface.

To apply the dressing, the seed is shaken with the dressing in a closed glass flask for 3 minutes.

3 batches of 12 grains of the barley are sown 2 cm deep in standard soil. 7 days after sowing, when the young plants have unfolded their first leaf, they are dusted with spores of *Erysiphe graminis* f. sp. hordei.

The plants are placed in a greenhouse at a temperature of about 20° C. and a relative atmospheric humidity of about 80% in order to promote the development of powdery mildew pustules.

Evaluation is carried out 7 days after the inoculation.

In this test, a clearly superior activity compound with the prior art is shown, for example, by the compounds according to the following preparation examples: 3 and 8.

Example C

Leptospaeria nodorum test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of Leptospaeria nodorum. The plants remain in an incubation cabinet at 20° C. and 100% relative atmospheric humidity for 48 hours.

The plants are placed in a greenhouse at a temperature of about 15° C. and a relative atmospheric humidity of about 80%.

Evaluation is carried out 10 days after the inoculation.

In this test, a clearly superior activity compared with the prior art is shown, for example, by the compounds according to the following preparation examples: 8 and 9.

Example D

Podosphaera test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the powdery mildew of apple causative organism (*Podosphaera leucotricha*).

The plants are then placed in a greenhouse at 23° C. and a relative atmospheric humidity of about 70%.

Evaluation is carried out 9 days after the inoculation.

In this test, a clearly superior activity compared with the prior art is shown, for example, by the compounds according to the following preparation examples: 3, 2, 4, 8, 9, 6 and 10.

Example E

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to the following preparation examples: 3, 9 and 8.

It is understood that the specification and examples are illustrative but not limitative of the present invention and that other embodiments within the spirit and scope of the invention will suggest themselves to those skilled in the art.

We claim:

1. A substituted azolylethyl oximinoalkyl ether of the formula $$R^1-CH-CH_2-N\diagup\genfrac{}{}{0pt}{}{N=}{\diagdown=N}$$
$$\underset{R^2}{\underset{|}{R^3-C}}-CR^4=N-OR^5$$

in which

R$^1$ is phenyl optionally monosubstituted or independently disubstituted by fluorine, chlorine, bromine, methyl, ethyl, methoxy, trifluoromethyl or trifluoromethoxy;

R$^2$, R$^3$ and R$^4$ each independently is hydrogen, methyl, ethyl, isopropyl, or any of the possibilities for R$^1$; and R$^5$ is hydrogen, methyl, ethyl, isopropyl, n-propyl, n-butyl, sec.-butyl, tert.-butyl, vinyl, allyl, propargyl, or phenyl or benzyl each of which is optionally monosubstituted or independently disubstituted by fluorine, chlorine, bromine, methyl, ethyl, methoxy, trifluoromethyl or trifluoromethoxy.

2. A compound according to claim 1, wherein such compound is 1-(2,4-dichlorophenyl)-1-(2-methoximinoethoxy)-2-(1,2,4-triazol-1-yl)-ethane of the formula

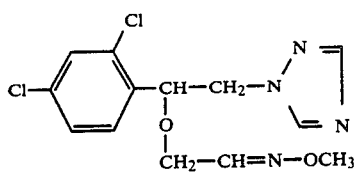

or an addition product thereof with an acid or metal salt.

3. A compound according to claim 1, wherein such compound is 1-(4-bromophenyl)-1-(2-methoximino-ethoxy)-2-(1,2,4-triazol-1-yl)-ethane of the formula

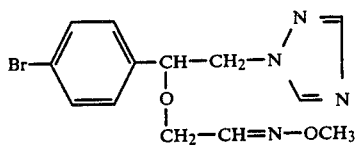

or an addition product thereof with an acid or metal salt.

4. A compound according to claim 1, wherein such compound is 1-(2,4-dichlorophenyl)-1-(2-methoximino-n-propoxy)-2-(1,2,4-triazol-1-yl)-ethane of the formula

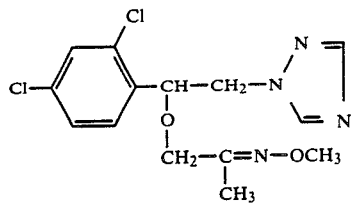

or an addition product thereof with an acid or metal salt.

5. A fungicidal composition comprising a fungicidally effective amount of a compound or addition product according to claim 1 in admixture with a diluent.

6. A method of combatting fungi which comprises applying to a fungus or a fungus habitat a fungicidally effective amount of a compound or addition product according to claim 1.

7. The method according to claim 6 wherein such compound is
1-(2,4-dichlorophenyl)-1-(2-methoximino-ethoxy)-2-(1,2,4-triazol-1-yl)-ethane,
1-(4-bromophenyl)-1-(2-methoximino-ethoxy)-2-(1,2,4-triazol-1-yl)-ethane,
1-(2,4-dichlorophenyl)-1-(2-methoximino-n-propoxy)-2-(1,2,4-triazol-1-yl)-ethane
or an addition product thereof with an acid or metal salt.

* * * * *